(12) United States Patent
Weisman et al.

(10) Patent No.: US 6,197,337 B1
(45) Date of Patent: Mar. 6, 2001

(54) THERAPEUTIC USES OF ABARELIX

(76) Inventors: Kenneth Weisman, 30 Springton Point Dr., Newtown Square, PA (US) 19073; Michael E. Goldberg, 20 Aspen Dr., Ivyland, PA (US) 18974

( * ) Notice: Subject to any disclaimer, the term of this patent is extended or adjusted under 35 U.S.C. 154(b) by 0 days.

(21) Appl. No.: 09/566,608

(22) Filed: May 9, 2000

Related U.S. Application Data

(60) Provisional application No. 60/133,481, filed on May 10, 1999.

(51) Int. Cl.[7] ............................... A61K 9/14; A61K 9/20; A61K 9/70
(52) U.S. Cl. ...................... 424/464; 424/422; 424/449; 424/489
(58) Field of Search ................................. 424/464, 449, 424/489, 422; 514/824

(56) References Cited

U.S. PATENT DOCUMENTS

| | | | |
|---|---|---|---|
| 5,574,011 | * | 11/1996 | Tien ........................................ 514/14 |
| 5,795,909 | * | 8/1998 | Shashoua et al. .................... 514/449 |
| 5,968,895 | * | 10/1999 | Gefter et al. .............................. 514/2 |

* cited by examiner

*Primary Examiner*—Thurman K. Page
*Assistant Examiner*—Charesse Evans
(74) *Attorney, Agent, or Firm*—Caesar, Rivise, Bernstein, Cohen & Pokotilow

(57) ABSTRACT

A method of decreasing atherosclerosis and its complications including but not limited to myocardial infarction, stroke and peripheral vascular disease wherein the method involves administering to a human or an animal an amount of abarelix sufficient to reduce atherosclerosis and its complications.

4 Claims, No Drawings

THERAPEUTIC USES OF ABARELIX

This application claims the benefit of the filing date of May 10, 1999 of Provisional Patent Applications Serial No. 60/133,481.

BACKGROUND OF THE INVENTION

There are many steps in the biosynthesis and utilization by the tissues of testosterone. Testosterone is made mostly in the testicles. A lesser amount is made in the adrenals. Production is stimulated by secretion of Gn RH or LHRH by the brain, which causes secretion of luteinizing hormone (LH) by the pituitary, which causes the testicles to make testosterone. Testosterone then flows into the blood stream and is absorbed by the target cells. Here it binds to a receptor and is transported into the cell and converted to dihydrotestosterone. This is bound and carried to the nucleus of the cell where it redirects cellular activity by turning on and off DNA. Hormonal manipulation is a term which refers to the reduction of testosterone or its effects by blocking any step in the above process in order to gain a desired effect. Until now the uses of hormonal manipulation include for example treating prostatic carcinoma, and treatment for baldness.

The present invention involves the use of hormonal manipulations in the prevention and treatment of cardiac events, including atherosclerosis, coronary heart disease, stroke and peripheral vascular disease. We have already discovered as reflected by our pending patent applications that certain 5-alpha reductase compounds are effective.

For instance, leuprolide acetate is one of the compounds we previously discovered being effective in the prevention of such cardiac events. Leuprolide acetate is a synthetic nonapeptide of naturally occurring gonadotropin-releasing hormone (GnRH or LH-RH), the chemical name is 5-oxo-L-prolyl-L-histidyl-L-tryptophyl-L-seryl-L-tyrosyl-D-leucyl-L-leucyl-L-arginyl-N-ethyl-L-prolinamide acetate salt sold under the trade name Lupron or Lupron Depot, as identified by U.S. Pat. No. 4,897,256, the entire disclosure is incorporated by reference herein, is known for use in the treatment of prostatic carcinoma. Leuprolide is a potent inhibitor of gonadotropin secretion known to decrease levels of LHRH, LH and Testosterone.

Another compound we previously discovered as being effective in the prevention of such cardiac events is goserelin acetate, a synthetic decapeptide analogue of LHRH or GnRH, is chemically described as an acetate salt of [D-Ser (Bu$^t$)$^6$ Azygly$^{10}$] LHRH. Its chemical structure is pyro-Glu-His-Trp-Ser-Tyr-D-Ser(Bu)-Leu-Arg-Pro-Azgly-NH2 acetate [C59H84N18O14 (C2H4O2) sold under the trade name Zoladex, as identified by the U.S. Pat. No. 5,510,460, the entire disclosure is incorporated by reference herein, is known for the use in treatment of prostatic carcinoma. Goserelin acetate is a potent inhibitor of gonadotropin secretion known to reduce levels of GnRH or LHRH, LH and Testosterone.

Finasteride, sold under the trade name Proscar by Merck and Co., is currently used in the treatment of benign prostatic hyperplasia, and is known to inhibit testosterone metabolism by blocking conversation of testosterone to dihydrotestosterone by blocking 5-alpha-reductase. Finasteride is yet another compound we previously discovered as being effective in the prevention of cardiac events.

Now, we have discovered the existence of abarelix which is a synthetic LHRH antagonist, the chemical name is N-Acetyl-3-(2-naphyl)-D-alanyl-4-chloro-D-phenylalanyl-3-(3-pyridyl)-D-alanyl-L-seryl-N-methyl-L-tyrosyl-D-aspaaginyl-L-leucy-N$^6$-isopropyl-L-lysyl-L-prolyl-D-alanylamide, manufacturer Praecis Pharmaceuticals Inc. is known for use in treatment of prostatic carcinoma. Abarelix is an inhibitor of gonadotropin secretion known to decrease levels of LHRH, LH, and Testosterone. Based on our studies of other 5-alpha reductase compounds, we believe that abarelix should be effective in preventing these cardiac events.

One of our studies of other 5-alpha reductase compounds was a retrospective study involving leuprolide acetate, goserelin acetate and finasteride was performed which compared the rates of patient reported heart attack in several groups: 1—control group of males entering the urology office for any routine complaint. 2—a group of prostate cancer patients treated with Leuprolide acetate, a LHRH inhibitor. 3—a group of prostate cancer patients treated with Goserelin acetate (Zoladex), a LHRH inhibitor. 4—a group of prostate cancer patients not treated with hormonal manipulation (neither leuprolide acetate or goserelin acetate). 5—a group of patients treated with finasteride (another form of hormonal manipulation). 6—all patients on LHRH inhibitors (group 2+group 3).

The patients on either leuprolide acetate or goserelin acetate were treated with the recommended doses indicated for the treatment of prostatic carcinoma, at either one or three month intervals depending on the preparation used. Leuprolide acetate was dosed at 7.5 mg monthly (single intramuscular injection) or at 22.5 mg at 3 month intervals (single intramuscular injection). Goserelin acetate was dosed at 3.6 mg monthly (subcutaneous injection) or at a dose of 10.8 mg at 3 month intervals (subcutaneous injection).

The various groups of office patients were given a questionnaire. In groups 2, 3 and 5 only those on drug for at least one year were considered. Cardiac event is defined as either the history of a heart attack or occurrence of coronary artery bypass or angioplasty. In control groups only events occurring in the 3 years prior to the questionnaire are charted. The results were as follows:

|  | No Patients | Cardiac Events | Subject Years | Events/Year |
|---|---|---|---|---|
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 (lupron acetate) | 28 | 1 | 118 | .00847 |
| Group 3 (goserelin acetate) | 25 | 1 | 62 | .0161 |
| Group 5- (finasteride) | 91 | 4 | 242 | .0165 |
| Group 6 (antiLHRH) groups 2 + 3 | 50 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (lupron acetate) and Total Control is 0.0253. 95% Confidence Interval for the difference between the proportions is 0.00514 and 0.0454. Patients treated with leuprolide acetate had fewer heart attacks than controls.

The observed difference between the proportions of Group 3 and Total Control is 0.0177. Patients treated with goserelin acetate (Zoladex) had fewer heart attacks than controls.

The observed difference between the proportions of Group 1 (Control) and Group 5 (finasteride) is 0.0186. 90% Confidence Interval for the difference between the proportions is 0.00103 to 0.0361. Patients treated with finasteride had fewer heart attacks than control.

It is believed that the use of abarelix will yield similar results.

The foregoing data demonstrates that by inhibiting testosterone metabolism atherosclerosis and cardiac events can be reduced. This has been demonstrated at two separate steps in the pathway, both by inhibiting LHRH and by inhibiting 5-alpha-reductase. Since abarelix acts to inhibit formation of LHRH it is believed that the use of abarelix will also result in a reduction of atherosclerosis and its complications; myocardial infarction, stroke, and peripheral vascular disease.

Without further elaboration the foregoing will so fully illustrate our invention that others may, by applying current and future knowledge, adopt the same for use under various conditions of service.

What is claimed is:

1. A method of decreasing atherosclerosis and its complications comprising administering to a human or animal an amount of abarelix sufficient to decrease atherosclerosis and its complications.

2. The method in claim 1 wherein the effective amount of abarelix is a 3 mg/kg/month intramuscular injection, administered monthly.

3. The method in claim 1 wherein abarelix is administered as a tablet, or as a part of a liquid solution or dispersion, or patch, or subcutaneous pellet, or any other method with the intent of accomplishing systemic absorption or the drug.

4. The method of claim 1 wherein the complications are selected from the group consisting of myocardial infarction, stroke and peripheral vascular disease.

* * * * *